(12) United States Patent
Gauthier, Jr. et al.

(10) Patent No.: US 6,637,255 B2
(45) Date of Patent: Oct. 28, 2003

(54) DAMPED PADDLE WHEEL FOR PLASMA CHAMBER SHOCK TUBE

(75) Inventors: Leo R. Gauthier, Jr., Timonium, MD (US); Angela L. Wesner-Barrios, Hanover, MD (US); David M. VanWie, Brookeville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/169,436

(22) PCT Filed: Jan. 8, 2001

(86) PCT No.: PCT/US01/00492
§ 371 (c)(1),
(2), (4) Date: Jun. 28, 2002

(87) PCT Pub. No.: WO01/50107
PCT Pub. Date: Jul. 12, 2001

(65) Prior Publication Data
US 2003/0066337 A1 Apr. 10, 2003

Related U.S. Application Data
(60) Provisional application No. 60/174,737, filed on Jan. 6, 2000.

(51) Int. Cl.[7] .......................... G01N 7/00; G01N 25/00; G01P 15/00
(52) U.S. Cl. .................. 73/31.05; 73/25.01; 73/514.13
(58) Field of Search ........................ 73/504.08, 514.12, 73/514.13, 147, 25.01, 54.31, 54.25, 12.08, 23.2, 31.05; 356/216

(56) References Cited

U.S. PATENT DOCUMENTS

| 182,172 | A | * | 9/1876 | Crookes | 356/216 |
|---|---|---|---|---|---|
| 1,321,736 | A | * | 11/1919 | Green | 73/54.31 |
| 3,983,749 | A | * | 10/1976 | Fletcher et al. | 73/147 |
| 5,311,774 | A | * | 5/1994 | Sava et al. | 73/147 |
| 6,311,549 | B1 | * | 11/2001 | Thundat et al. | 73/54.24 |

FOREIGN PATENT DOCUMENTS

SU 720348 3/1980 ................ 21/24

* cited by examiner

Primary Examiner—Hezron Williams
Assistant Examiner—John C Hanley
(74) Attorney, Agent, or Firm—Francis A. Cooch

(57) ABSTRACT

A damping gyrometer comprised of at least two and preferably four rotating paddles attached to a common central elevated low-friction pivot point via rising radial arms. A stand with a concave glass element provides a low-friction support as a pivot point seat for the pivot point. All elements of the apparatus are non-conductive. Once set into motion, the only force acting on the gyrometer are the pivot point friction and the damping effects of the medium in which it spins. A laser beam and photodetector (or alternatively a laser displacement sensor), along with customized software algorithms are used to measure the rotational rate and, hence, the deceleration rate of the apparatus which can then be used to determine properties of the medium in which it spins, including changes in density, pressure, and temperature. The measurement can also be directly related to the electron density in the case of weakly ionized gases.

9 Claims, 3 Drawing Sheets

DAMPED PADDLE WHEEL FOR PLASMA CHAMBER SHOCK TUBE

CROSS-REFERENCE TO RELATED APPLICATIONS

This application claims the benefit of prior filed co-pending U.S. Provisional Patent Application No. 60/174,737, filed on Jan. 6, 2000.

FIELD OF THE INVENTION

The present invention relates generally to sensors for measuring the properties of a gaseous medium and, more specifically, to a damping gyrometer for measuring the properties, e.g., temperature, of a gaseous medium based on the measured damping effects that are principally caused by thermally induced viscosity changes.

BACKGROUND OF THE INVENTION

Many recent experiments involving the study of the interaction of weakly ionized gases and moving bodies have yielded anomalous observations that are not explained satisfactorily according to currently understood phenomena. The fractional degree of ionization needed to see the effects are on the order of $10^{-6}$. Most of these effects are easiest to observe under highly energetic flow conditions. The most striking and potentially the most valuable effect concerns measurable changes in shock profiles, shock velocities and shock intensities.

Modified shockwaves can alter the way that an air vehicle interacts with its environment. In a dynamic flow setting where a vehicle surface is interacting with the weakly ionized gas, these effects can be translated into drag and surface heating rate variations that potentially afford an important mechanism for solid-state electronic control. The long-range goal of the study of these interactions is to understand the processes sufficiently to be able to apply them to optimizing the systems-level performance of aerodynamic vehicles.

Although the most striking measurable effects are seen under highly energetic flow conditions, these conditions are inherently difficult to study when trying to understand the basic physical processes that underlie the observed system behavior. The conditions are highly unsteady and measurements require the use of high-speed data acquisition systems. In addition, the electronic mechanisms for producing the weakly ionized gas can introduce excessive noise into the measurement system.

On a systems level, there is a price to be paid for the observed aerodynamic effects in terms of the input power needed to alter the medium. Some portion of the observed effects can often be attributed to the natural Joule-heating of the medium. It is necessary to separate the heating effects from "other" energy exchange mechanisms to understand if there is any novel aspect that is attributable to the ionization. Possible "other" mechanisms include non-equilibrium energy exchange between translational, vibrational, rotational and electronic states, storage of potential energy within transient plasma structures or electric double layers, and ion-acoustic interactions. To reduce the number of variables, a shock tube apparatus was used to study the processes associated with propagating shocks in a weakly ionized gas in a manner that was largely independent of boundary layer interactions.

In an experimental setup, the shock tube consisted of a high-pressure driver section and low-pressure section separated by a diaphragm. Gas was supplied through a bottle system. Air was usually used as the source gas but in some tests, carbon monoxide (CO) was also used to seed the gas for spectral signatures. Within the low-pressure section, copper anodes and nickel cathodes, mounted on the upper and lower surfaces, were used to create a uniform electrical discharge that was transverse to the shockwave propagation direction. The maximum available current was four amperes provided in constant current mode allowing current densities up to ~150 $A/m^2$.

Two laser beams were passed through the driven section and onto photodetectors to detect the passage of the shockwave after the diaphragm was burst. The photodetectors were thus able to measure both velocity and intensity of propagating shocks.

A previously reported main conclusion from the shock tube measurements was that the shock propagation velocity increased in proportion to the current density, a result that was not inconsistent with purely thermal effects. (See, Van Wie D. M., Wesner, A. L., and Gauthier, L. R., Jr., "Shock Wave Characteristics Measured in Gas Discharges," AIAA Paper 99-4824, November 1999.) However, since the gas temperature was difficult to measure during the discharge, other possible effects could not be ruled out.

To further resolve the effects, new devices and methods were needed to characterize the weakly ionized plasma and the unionized gas in the absence of a propagating shock.

SUMMARY OF THE INVENTION

The damping gyrometer of the invention can be used to measure minute forces exerted on a rotating body placed within the shock tube medium. In one embodiment, the damping gyrometer comprises at least two and, preferably, four rotating disks or paddles symmetrically mounted to a common central elevated low-friction pivot point via rising radial arms. The pivot point is the single point of mechanical support for the rotating apparatus/means. A stand with a concave glass element/lens provides a low-friction support as a pivot point seat for the pivot point. All elements of the apparatus are non-conductive.

Once set into motion, the only force acting on the gyrometer are the pivot point friction and the damping effects of the medium in which it spins. A laser beam and photodetector (or alternatively a laser displacement sensor), along with customized software algorithms are used to measure the rotational rate and, hence, importantly, the rotational rate of change overtime or deceleration rate of the apparatus. The deceleration of the damping gyrometer can then be used to determine properties of the medium in which it spins, including changes in density, pressure, and temperature. The measurement can also be directly related to the electron density in the case of weakly ionized gases.

In the present embodiment, short air blasts through a hollow tube are used to impart momentum to the rotating part of the damping gyrometer and acquired data are post-processed and interpreted offline. In another embodiment, the same laser used to determine rotational rate by extracting the paddle location measurements can be used to impart momentum to the rotating means. A microprocessor can be used to generate the time/frequency data and to calculate the parameters of the medium that are being measured. In this embodiment the rotating apparatus is placed within a chamber holding the medium of interest and can be set in motion and non-contact measurements taken through a window into the chamber by purely optical means.

DETAILED DISCLOSURE OF THE INVENTION

Figure 1:
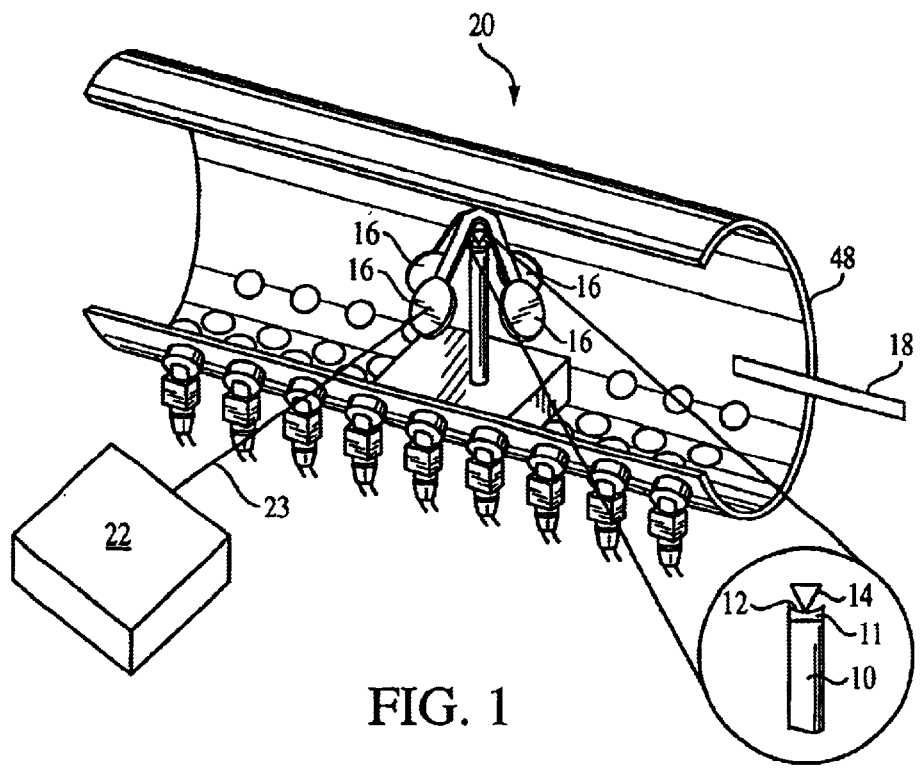
FIG. 1 illustrates the damping gyrometer of the invention within a plasma chamber/shock tube and further shows an exploded view of the pivot point seat portion of the invention.

The damping gyrometer of the invention is a miniature device that is used to measure minute damping forces exerted on a balanced low-friction single pivot spin mechanism placed within the gaseous medium. As shown in FIG. 1, the gyrometer comprises a vertical fiberglass stand 10 that supports a concave glass lens 11, forming the seat 12 for a single pivot point rotating mechanism. The rotating mechanism is comprised of a single insulative inert pivot point 14 that supports four (can be two or more) symmetrically mounted paddles 16 that extended radially outward and downward from the center. Both fiberglass and teflon paddles of the same size and shape can be used. However, the lower density of the fiberglass paddles yield the best data. The stability of the rotating mechanism is due to the low center of gravity beneath the pivot point.

Figure 2:
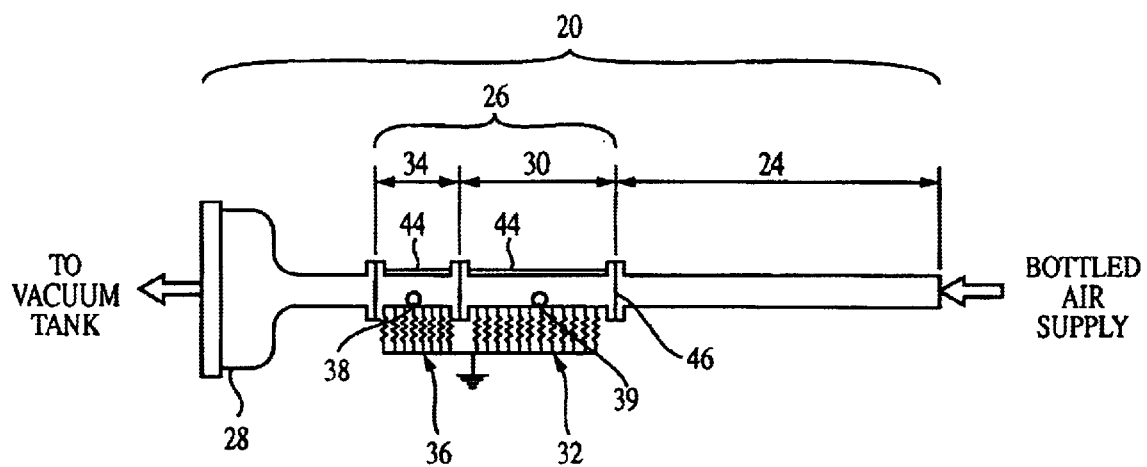
FIG. 2 is a schematic of a shock tube (dimensions in mm).
Figure 3:
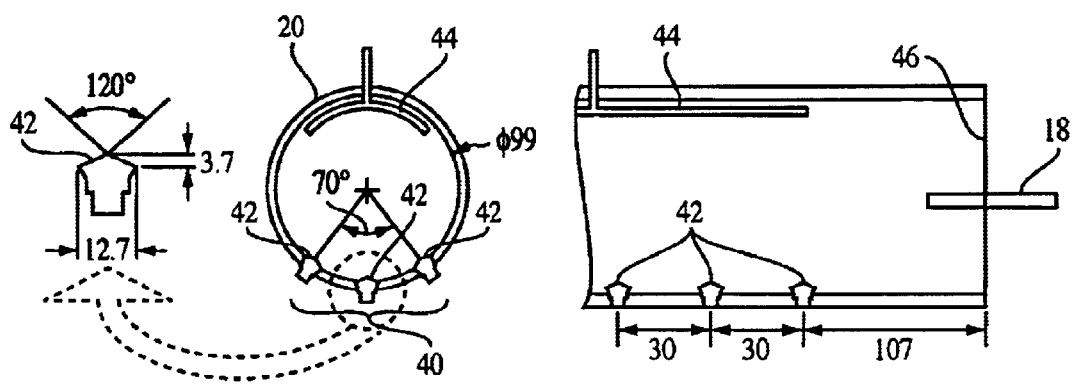
FIG. 3 illustrates the electrode geometry in the shock tube (dimensions in mm).

The gyrometer can be set in motion by a burst of air provided by a pluggable hollow dowel 18 (see FIGS. 1 and 3) that penetrates the shock tube 20 (see FIGS. 1–3). At very low pressures the gyrometer can spin for up to fifteen minutes after an initial revolution rate of approximately four rotations per second. As shown in FIG. 1, a laser displacement sensor 22 is used to measure the rotational rate of the gyrometer by passing the beam 23 through the Pyrex sidewall of the shock tube and reflecting the beam off the passing addles.

A Matlab routine has been written to convert the measured displacement sensor data into ascribed frequency versus time data for analysis. A measurable and repeatable retarding torque was found to act on the gyrometer whenever the plasma state was established. An interpretation of this damping effect based on thermally induced gas viscosity changes yields gas temperature measurements.

A schematic of the shock tube 20 used to perform temperature measurements is shown in FIG. 2. The shock tube is 99 mm in diameter and consists of a 660 mm long driver section 24, 768 mm driven section 26 and a receiver volume 28. The driven section was constructed in two sections made of Pyrex. The upstream section 30 was 508 mm long and contained a 12×3 cathode array 32. The downstream section 34 is 260 mm long and contained 7×3 cathode array 36. The downstream section also contained a pair of 25.4 mm diameter observation windows 38.

Additional details on the electrode configuration are shown in FIG. 3. The cathode 40 consisted of an array of conical Ni-200 electrodes 42. The axial spacing of the electrodes is 30 mm and the angular spacing is 35°. The conical tip is 120° total included angle, and is 12.7 mm in diameter with the tip 3.7 mm above the surface of the Pyrex tube. The anode 44 consists of two copper plates located along the upper surface of the driven section. The anode in the upstream driven section is 355.6 mm long with an arc-length of 67 mm. The anode in the downstream driven section is 184 mm long with an arc-length of 67 mm. The anode and cathode electrodes begin 107 mm downstream from the diaphragm.

The discharge was generated using one or two Universal Voltronics Model BRC-5-2000R-STD-3PH-200V DC power supplies in parallel. Each power supply was operated in a constant current mode with the capability of producing up to 5000 V and 2 A.

Prior to investigating shock propagation characteristics in the plasma, a characterization of the undisturbed plasma was undertaken. Measurements were taken of the rise and fall time of the discharge current waveforms both on the cathodic and the anodic side of the test chamber. Measurements indicate the power supply established a steady discharge within 20 milliseconds after turn-on. The waveforms showed a characteristic current spike of 1 millisecond duration and 2–5 times the steady state value during the plasma turn-on time. Extinction of the discharge current occurred in approximately 1 millisecond. The plasma was homogenous in appearance.

The shock tube has two transverse diagnostic ports 38, 39 which are used to direct the infrared energy beam through KBr windows. A globar not shown is used to provide the infrared beam. In tests where a CO seed was used, a small needle valve was used to allow the CO gas into the shock tube prior to a test.

To test the damping gyrometer, it was placed into the shock tube near the upstream electrodes. A large rubber diaphragm 46 in FIGS. 2 and 3 was used to seal the tube. A hollow fiberglass tube 18 passed through the rubber diaphragm was used to provide the short burst of air needed to set the gyrometer in motion. A laser displacement sensor (LAS 8010V) 22 was used to measure the distance to each paddle of the gyrometer as it passed by aiming the laser through the Pyrex sidewall 48 in FIG. 1 of the shock tube. Several oscilloscopes were used to acquire data from the laser displacement sensor. It was necessary to sample the laser displacement sensor at least once every millisecond to be able to resolve the paddle position.

A Matlab routine processed the output from the laser displacement sensor and produced a time/frequency series corresponding to the state of the gyrometer as it spun down. The need for 1 millisecond sampling rate and long spin down times (up to several minutes) created large data files during measurements that covered a significant portion of a spin (256 seconds). For each paddle, adjacent times of passage $T_i$ and $T_j$ were used to compute an ascribed time and ascribed frequency. The ascribed time is $(T_i+T_j)/2$ and the ascribed frequency is $1/(T_j-T_i)$. The time/frequency series were then converted into phase plane plots that showed the relationship between the frequency and its derivative.

The greatest difficulty encountered during the gyrometer tests was eliminating external influences. The most problematic was air leakage around the electrodes and other rig openings as the plasma heated up. The mass of the fiberglass paddles of the damping gyrometer was only 7.95 grams. Fortunately, when the data was processed, the leakage effects were revealed by anomalies such as the gyrometer increasing its frequency for short periods of time. Data sets with clear leakage effects were not used.

It should also be pointed out that the damping gyrometer used in these experiments was much more massive than radiometer type devices investigated by others that depend on the thermal effects caused by incident radiation to impart motion In any event, the heating of the damping gyrometer itself was symmetrical by construction and thus heating effects on the gyrometer itself should not impart net motion. The laser used by the laser displacement sensor was small enough (1 mW) to preclude heating or the imparting of momentum.

The damping gyrometer within the shock tube is shown in FIG. 1. The gyrometer exploits properties of fluids in the creeping flow regime, best described by exceedingly low Reynolds number. Computing the Reynolds numbers for the flow about the gyrometer paddles based on the geometry of the gyrometer produces the following range for revolution rates (f) from 1–3.5 revolutions per second and pressures from 1 to 10 Torr.

$$Re = \frac{\rho UD}{\mu} = \frac{2\pi r f P D}{RT\mu}$$

where,
f is the rate of revolution=1–3.5 Hz
r is the moment arm=1 in (0.0254 m)
P is the pressure range=0.0193–0.193 psi
D is the paddle diameter=1 in (0.0254 m)
R is the gas constant for air=1716 ft-lb/(slug R)
T is gas temperature=530 R (294 K)
$\mu$ is the viscosity=2.11E-5 lb-s/ft$^2$
U is the paddle velocity=$2\pi r f$ This yields Reynolds Number of:
0.006<Re<0.3

This range of Reynolds numbers is within the flow regime known as creeping motion or flow. Stokes' solution for an immersed sphere employing creeping motion led to several extraordinary properties of this type of flow:
1) The streamlines and velocities are entirely independent of the fluid viscosity.
2) The streamlines possess perfect fore-and-aft symmetry.
3) The local velocity is everywhere retarded from its freestream value.
4) The freestream disturbance extends to enormous distances.

The most extraordinary result found was for the total drag force developed by integrating the pressure and shear around the surface.

$$F=6\pi\mu UD$$

Note that the drag force on the sphere (and any similar body within creeping flow) is independent of tie fluid density.

In principle, a Stokes flow analysis is possible for any three-dimensional body shape. Contained within these solutions is the exact result for a disk normal to the freestream.

$$F=16\mu UD$$

Again note that this result is independent of the freestream gas density.

Thus, the drag on the gyrometer paddles should be directly proportional to the viscosity, the paddle diameters, and the paddle rotational rates.

$$F_{paddles} \propto \mu U_{paddles} D$$

This translates into a retarding torque on the gyrometer given by the following equation.

$$T_{Aerodynamic} \propto \mu UD$$

The total torque on the body is composed of the aerodynamic drag, following the functional form given above, and the torque from the pivot drag.

$$T_{Total}=T_{Aerodynamic}+T_{Friction}$$

The torque from the friction is proportional to the pivot radius and the material coefficient of friction. It is only necessary that it is small and not sensitive to temperature variations.

$$T_{Friction} \propto r_{Pivot} \mu_k$$

Kinematics dictates that the angular deceleration, $\alpha$, is given by the following formula:

$$\alpha = \frac{T_{Total}}{I}$$

where, I is the damping gyrometer moment of inertia. Thus, $$\alpha \propto \mu(T)U + const$$

Assuming the temperature is constant, then, $$\alpha \propto U + const$$

Given that U, the paddle velocity, for the gyrometer is a constant times the rotational rate, the following relational function for the derivative of the gyrometer rotational frequency is seen.

$$-f'=af+const$$

Figure 4:
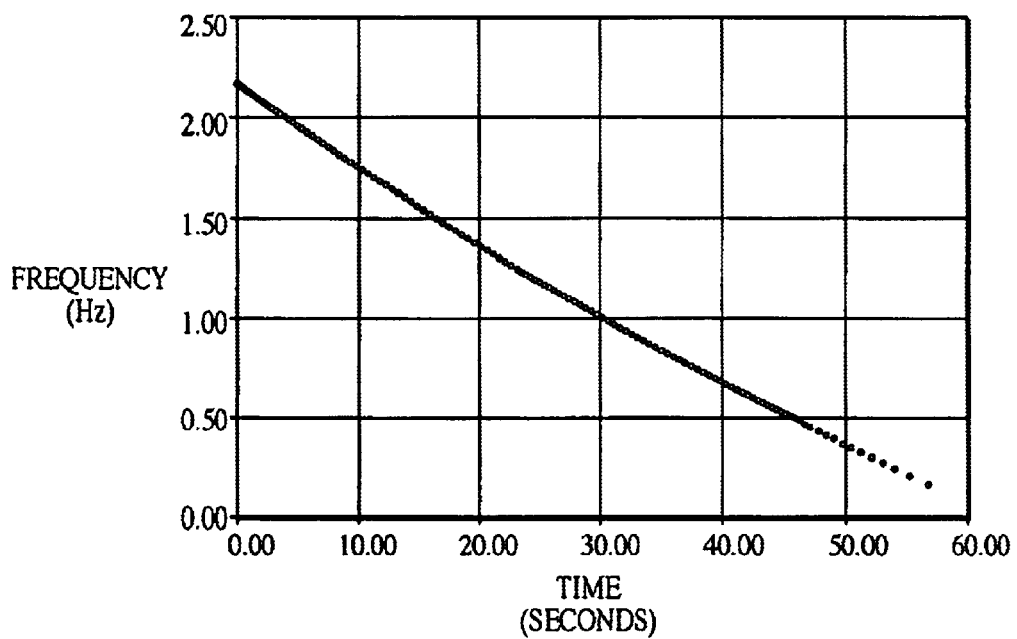
FIG. 4 illustrates a plot of typical frequency versus time spin-down for the gyrometer of the invention (for current density 26 A/m$^2$).
Figure 5:
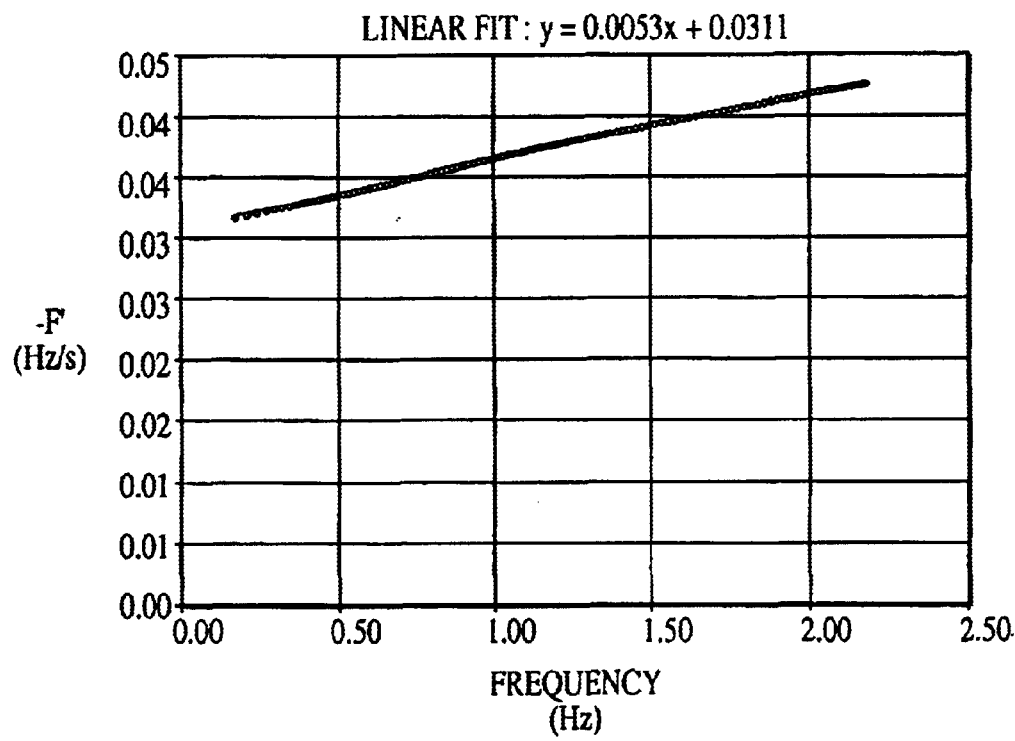
FIG. 5 illustrates a phase plane plot corresponding to the plot of FIG. 4.

Finally, since the proportionality constant, a, is directly related to the temperature through the gas viscosity, the slope of the line relating f and $-f'$ for a single spin (needed to insure a uniform friction) is an indirect measure of the gas temperature. FIG. 4 shows a typical frequency versus time spin down plot for the gyrometer (for current density 26 A/m$^2$). FIG. 5 shows the corresponding phase plane plot.

Figure 6:
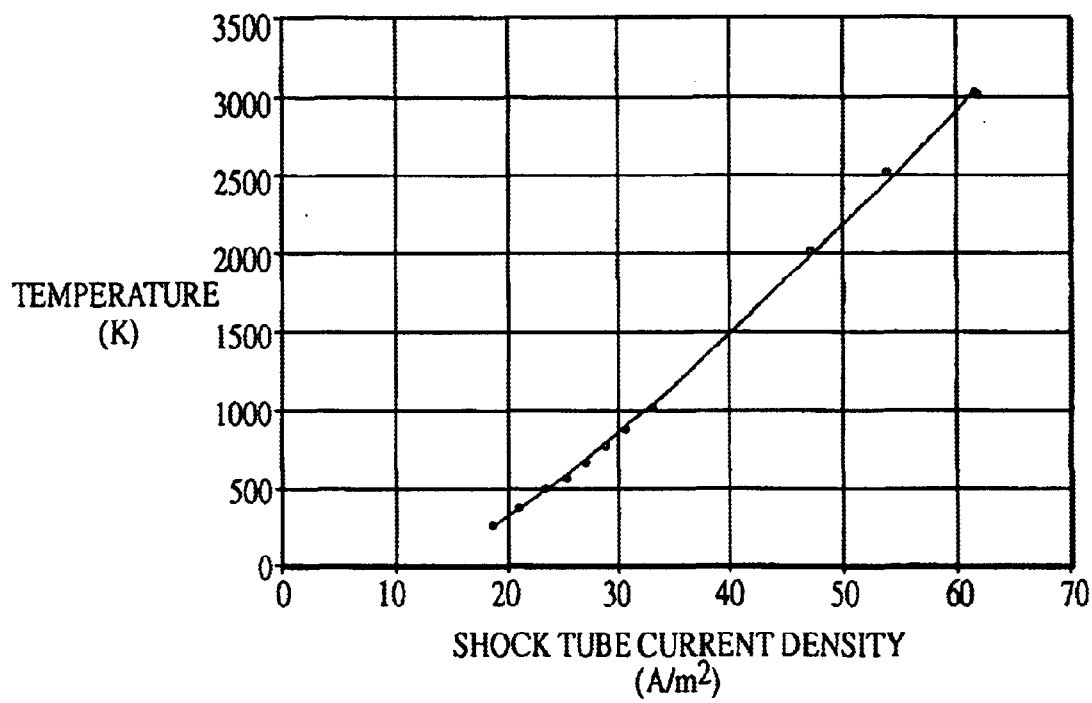
FIG. 6 illustrates the relationship between current density and gas temperature in the shock tube based on the measurements with the damping gyrometer of the invention and theory.

The proportionality constant, a, between the gyrometer frequency f and its negative derivative ($-f'$) was found to increase with increasing current density in the shock tube. Theory ties this to the gas temperature. FIG. 6 shows the relationship between current density and gas temperature in the shock tube based on the measurements with the damping gyrometer and the theory. The temperature corresponding to the measured gyrometer characteristics at the 40 A/m$^2$ current density as used during the measurements made using a fast scanning Fourier Transform Infrared Spectrometer (FTIR) yields 1435 K.

Possible electrical effects were not addressed during the discussion above. Only insulative materials were used in the construction of the gyrometer. The paddles were made of fiberglass and the pivots that were used were made of either boron nitride or fiberglass. A glass tip was used with the fiberglass pivot since early testing showed that the pivot point friction increased greatly under heating when the fiberglass was used as the tip.

Electrostatic influences were found to be negligible based on comparison of spin downs at atmospheric pressure with and without 5 KV applied across the electrodes. No current flow occurred during these tests due to the higher insulative properties of the air at the higher pressure. Based on comparison of the spin down plots, any induced electrostatic charges were balanced and did not significantly affect the motion of the device. While reactive effects due to the paddles disturbing the current flow cannot be completely ruled out, the agreement of the thermal interpretation of the device with the spectroscopic measurements indicates that the temperature is the dominant variable that controls the gyrometer response.

The calculation of the expected gas temperature based on the measured shock velocity within the gas was accomplished using the standard one-dimensional unsteady shock tube equations. This is a simplified analysis and does not include any effects from non-uniform temperature distributions known to be present within the ionized gas, the time required to initially develop or accelerate the shock, etc. Also, a complication is introduced since the shock initially forms within a cold gas and then travels into a region of higher temperature (the region of gaseous ionization).

Using measured values of the shock propagation velocity in cold flow (800 m/s) and knowing the cold gas temperature (300 K) and pressure (1 Torr), the strength of the shock and all aerodynamic properties behind the shock are calculated for the initial development of the shock within the cold region. When the shock enters the region of elevated temperature, the shock accelerates and an expansion wave is reflected from the boundary.

A second shock calculation, similar to the initial calculation, is performed. This calculation is performed iteratively, as the driver gas has a velocity, induced by the passage of the non-accelerated shock. Knowing the measured shock velocity within the plasma (970 m/s) at a current density of 40 A/m$^2$, a plasma temperature was assumed, and the pressure values on both sides of the contact surface were calculated. If the pressures on either side of the contact surface did not match, the assumed plasma temperature was adjusted until the pressure difference across the contact surface reached zero. To produce a shock velocity of 970 m/s within the plasma, a temperature of 1135 K was calculated with this method. Table III is a comparison of the gas temperature results from various approaches at a current density of 40 A/m$^2$.

TABLE III

Summary of Gas Temperature Results for 40 A/m$^2$ Current Density

| Method | Pressure (Torr) | Temperature (K.) |
| --- | --- | --- |
| FTIR P & R branches | 3 | 1335 |
| FTIR P Branch | 3 | 1453 |
| Damping Gyrometer | 1–10 | 1435 |
| Lossless 1D Analysis | 1 | 1135 |
| Thermocouple | 1–10 | 560 |

A temperature of 1400 K was found to produce a shock velocity of ~1060 m/s. This is less than 10 percent error over the measured shock velocity in the ionized gas. A temperature of 1500 K yields a shock velocity of 1090 ms, which is less than 13 percent lower. Thus, the damping gyrometer of the invention yielded a very similar temperature measurement for the same current as did FTIR which temperature measurement was also consistent with a lossless one-dimensional computation based on the measured shock velocity changes that were observed previously.

What is claimed is:

1. A damping gyrometer for determining a property of a gaseous medium comprising:

a vertical stand comprised of an insulating and chemicaly inert material;

a rotating means, comprised of an insulating and chemically inert material, mounted on the stand, the rotating means comprising:
a pivot point; and
at least two paddles, the paddles being symmetrically mounted to the pivot point and extending radially outward and downward therefrom;

means for setting the rotating means in motion;

means for measuring the rate of rotation of the rotating means to determine the deceleration of the rotating means; and means for determining the property of the gaseous medium using the deceleration of the rotating means.

2. The gyrometer as recited in claim 1, further comprising a pivot point seat supported by the stand, the pivot point of the rotating means being mounted on the pivot point seat.

3. The gyrometer as recited in claim 2, the pivot point seat comprising a concave glass lens.

4. The gyrometer as recited in claim 1, wherein the paddles are fiberglass.

5. The gyrometer as recited in claim 1, wherein the tip of the pivot point is glass.

6. The gyrometer as recited in claim 1, the setting in motion means comprising a hollow tube for supplying a burst of air.

7. The gyrometer as recited in claim 1, the setting in motion means comprising a laser for supplying a laser beam.

8. The gyrometer as recited in claim 1, the means for measuring the rate of rotation comprising a laser.

9. A method for determining a property of a gaseous medium comprising the steps of:

placing a rotating means, comprised of an insulating and chemically inert material, in the gaseous medium;

setting the rotating means in motion;

measuring the rate of rotation of the rotating means to determine the deceleration thereof; and determining the property of the gaseous medium using the deceleration.

* * * * *